United States Patent
Donovan et al.

[11] Patent Number: 5,695,777
[45] Date of Patent: Dec. 9, 1997

[54] ABSORPTIVE WOUND DRESSING FOR WOUND HEALING PROMOTION

[75] Inventors: Maura G. Donovan, St. Paul; James R. Keogh, Maplewood; Carolann M. Holmblad, Cambridge, all of Minn.

[73] Assignee: Medtronic, Inc., Minneapolis, Minn.

[21] Appl. No.: 241,120

[22] Filed: May 10, 1994

[51] Int. Cl.$^6$ .............................. A61K 9/70; A61L 15/00
[52] U.S. Cl. ..................... 424/443; 424/445; 424/447; 424/448; 424/449
[58] Field of Search ........................... 424/443, 445, 424/447, 448, 449

[56] References Cited

U.S. PATENT DOCUMENTS

| | | | |
|---|---|---|---|
| 4,060,081 | 11/1977 | Yannas et al. | 128/156 |
| 4,226,232 | 10/1980 | Spence | 128/156 |
| 4,552,138 | 11/1985 | Hofeditz et al. | 128/156 |
| 4,661,099 | 4/1987 | von Bittera et al. | 604/290 |
| 4,746,514 | 5/1988 | Warne | 424/445 |
| 4,760,131 | 7/1988 | Sundsmo et al. | 530/356 |
| 4,785,079 | 11/1988 | Gospodarowicz et al. | 530/399 |
| 4,979,941 | 12/1990 | Ogle, II | 604/82 |
| 4,979,946 | 12/1990 | Gilman | 604/307 |
| 5,106,629 | 4/1992 | Cartmell et al. | 424/445 |
| 5,112,618 | 5/1992 | Cartmell et al. | 424/443 |
| 5,154,928 | 10/1992 | Andrews | 424/445 |
| 5,204,110 | 4/1993 | Cartmell et al. | 424/443 |
| 5,229,172 | 7/1993 | Cahalan et al. | 427/536 |
| 5,238,685 | 8/1993 | Wren | 424/445 |
| 5,260,066 | 11/1993 | Wood et al. | 424/447 |
| 5,264,218 | 11/1993 | Rogozinski | 424/445 |
| 5,298,015 | 3/1994 | Komatsuzaki et al. | 602/46 |
| 5,322,695 | 6/1994 | Shah et al. | 424/448 |

*Primary Examiner*—Thurman K. Page
*Assistant Examiner*—Sharon Howard
*Attorney, Agent, or Firm*—Thomas F. Woods; Harold R. Patton

[57] ABSTRACT

A wound dressing for use with exuding wounds includes (a) an outer vapor permeable layer permitting transpiration of fluid from the dressing; (b) an intermediate layer of hydrogel adapted for absorbing wound exudate; (c) a wound-contacting layer for separating the intermediate hydrogel layer from the wound; (d) wicking means associated with the wound-contacting layer for conducting exudate from the wound to the hydrogel; and (e) a therapeutic agent retained in the dressing by the wound-contacting layer.

10 Claims, 2 Drawing Sheets

5,695,777

ABSORPTIVE WOUND DRESSING FOR WOUND HEALING PROMOTION

BACKGROUND OF THE INVENTION

This invention is in the fields of medicine and surgery. More particularly, it concerns an absorptive wound dressing that is designed to prevent pooling of wound exudate and to promote wound healing.

The observation that occlusive dressings provide a moist wound healing environment and cause a superior healing response is considered a major advance in the field of dermal and epidermal repair. The current occlusive dressings can be organized into several categories: transparent adhesive films (primarily polyurethanes), non-transparent adhesives (hydrocolloids), semi-transparent non-adhesives (hydrogels), and non-transparent non-adhesives (foams). The three main advantages of occlusive dressings are that they speed healing of acute wounds, stimulate healing of chronic non-healing wounds and reduce wound pain.

When applied to chronic wounds, occlusive dressings induce an exudation, produce a debridement (autolytic debridement), stimulate development of granulation tissue and in many cases induce complete healing of the chronic wound. There have been many proposed mechanisms for the effectiveness of these dressings. For example, it has been theorized that the retention of exudate under the dressing is helpful because of the presence of many growth factors in the fluid. It has also been proposed that by preventing drying and crust formation, occlusive dressings facilitate epidermal migration and resurfacing.

Currently, most technologic innovations in the occlusive dressing field relate to the development of dressings that are better able to absorb, transmit or otherwise manage the exudate. In chronic wounds, the exudative phase can last from one to several weeks. During this time, hydrocolloid dressings often breakdown on the wound. As a consequence, hydrocolloid treated wounds generally require additional cleansing during dressing changes. Traditional hydrogel dressings, while absorptive, can cause wound maceration thereby delaying healing. For example, in U.S. Pat. No. 5,204,110 issued to Cartmell, a burn dressing is described which has a hydrogel material that is applied to the wound surface. Due to the hydrophilic nature of the hydrogel, it is able to take up the water component of the exudate. However, since the adsorbed moisture lies in continuous, direct contact with the wound, wound maceration can occur. This issue has been addressed in U.S. Pat. No. 4,979,946 to Gilman by employing a moisture permeable sheet between the wound and the absorbent hydrogel layer or in U.S. Pat. No. 4,746,514 to Warne by placing the hydrogel into a semi-permeable membrane.

While occlusive dressings seal off the wound and thereby have improved management of infectious bacterial agents, therapeutic substances have been added to wound dressings and to hydrogels in wound dressings to provide additional bacterial control and to provide other therapeutic benefits. For example, in U.S. Pat. No. 5,260,066 to Wood, et. al., therapeutic agents are used as additives to a PVA cryogel bandage for controlled release of those substances. Wood et al cites therapeutic substances which are incorporated herein by reference, including: antibiotics inhibiting cell wall formation, disrupting DNA metabolism, inhibiting protein biosynthesis, altering cellular membrane functions, quinolones, antimicrobials, antipathogenic polypeptides, antibacterial and antifungal agents, antiviral agents, steroidal and non-steroidal anti-inflammatory drugs, anti-cancer drugs, anti-clotting agents, anti-tissue damage agents, immune modulators, monoclonal and polyclonal antibodies, hormones, immunosuppressives, thrombolytic agents, vitamins, amino acids, prostaglandins, enzymes, buffers and salts, anions, preservatives, vasodilators; antiarrhythmic agents, cardiotonics, antihypertensives, local anesthetics, hypotensive diuretics, hypnotics and sedatives, central nervous system agents, antitubercular agents, post-cerebral embolism agents, and antiulcer agents. However, administering such a battery of drugs to a wound via a wound dressing raises significant technical, regulatory and administrative problems that conventional wound dressings have heretofore avoided.

It is therefore broadly the object of this invention to provide an improved occlusive dressing for use in treating wounds with differing etiologies. An advantage of the invention lies in the use of an absorptive hydrogel which does not directly contact the wound. Additionally, the hydrogel in the improved dressing may be tailored to the needs of specific wounds through the inclusion of therapeutic agents such as antimicrobials which remain largely undelivered to the wound site and yet provide an environment which inhibits microbial growth. Similarly, the wound contacting surface can be further modified to include therapeutic agents such as biologically active substances to promote healing which are bound to the structure of the wound dressing.

SUMMARY OF THE INVENTION

The absorptive wound dressing of the invention in its broader aspects comprises a laminar structure of three layers a) a porous medical grade polymer material layer that is placed in direct contact with the wound and which is characterized as being wound friendly and able to wick or otherwise transfer exudate away from the wound to the hydrogel, b) an intermediate layer of a hydrogel composition formulated to be highly absorptive of the exudate, and c) an outer oxygen and vapor permeable layer for transpiration of at least part of the fluid diffusing through the dressing. The outer layer may be of a larger surface area than the other layers so as to include a peripheral skin-contacting adhesive on the underside thereof surrounding the wound area and facilitating contact and covering of the wound.

The wound-contacting layer effects the separation of the intermediate hydrogel layer from the wound and includes wicking means (i.e. polymeric fibers which can be joined together to make up the wound-contacting layer) for conducting exudate from the wound to the hydrogel. A therapeutic agent is included in the dressing and is substantially retained in the dressing by the wound-contacting layer. This can be accomplished by incorporating the therapeutic agent in the hydrogel since the hydrogel is separated from the wound. It can also be accomplished by placing the therapeutic agent in the wound-contacting layer in a bound state (i.e. biologically active molecules bound to the fibers associated with the wound-contacting layer). The molecules are preferably bound covalently to provide the most secure attachment. In an especially preferred aspect of the invention, a growth factor or fibronectin is provided as the therapeutic agent.

DETAILED DESCRIPTION OF THE INVENTION

Figure 1:
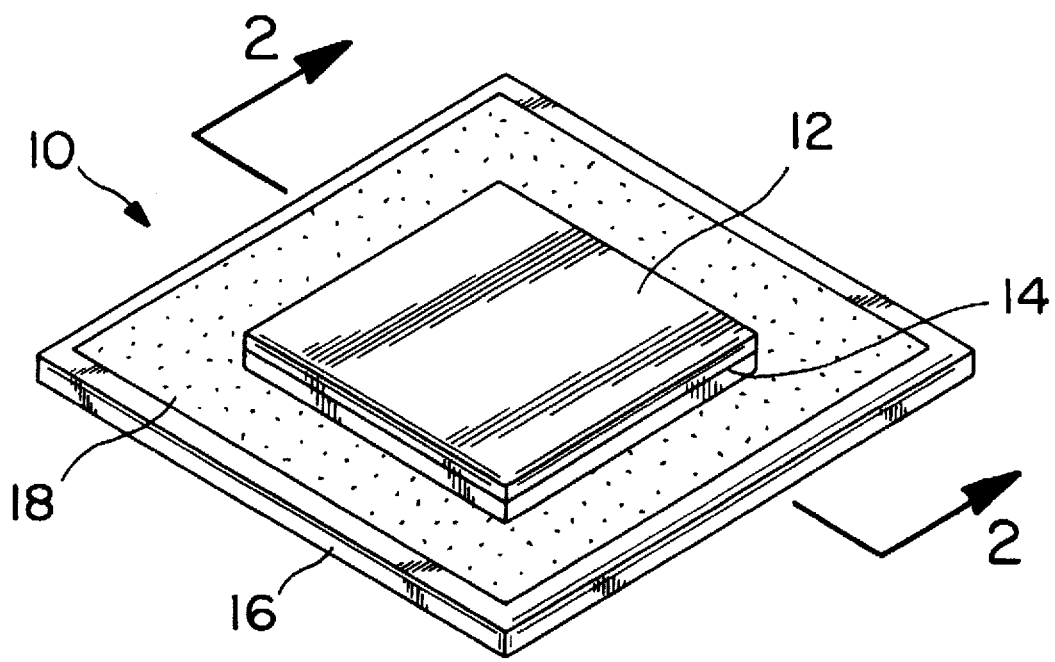
FIG. 1 is a perspective view showing the bottom or underside or surface of the wound dressing adapted to be placed on the skin and to cover the wound.
Figure 2:
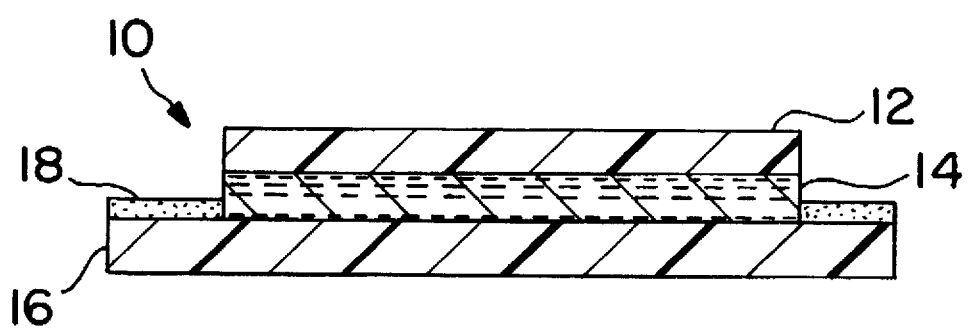
FIG. 2 is a sectional view taken along line 2—2 of FIG. 1.

The wound dressing of the invention is illustrated in FIGS. 1 and 2 which show a laminar structure generally designated 10 comprised of three layers 12, 14 and 16.

Layer 12 contacts the wound and consists of the wound friendly polymer which conducts exudate away from the wound and separates the wound from other components of the dressing. The layer may for example, be a porous fabric or mesh such as the screen fabrics or filter fabrics of polyethylene, polypropylene, nylon or polyester. Any of a variety of polymeric materials may be used. The choice of suitable material and pore size or the like for transfer in this layer will be dictated by the need to prevent the absorbent hydrogel from expanding through the layer. In addition, the material should be flexible, soft, conformable, non-irritating, non-sensitizing, and non-cytotoxic. Table 1 summarizes the properties of a preferred specific thermally bonded spun web polypropylene material that has been found particularly suitable for use as layer 12. This material has wicking characteristics which have been found to be especially desirable in wound dressings to be used on wounds which require draining. Other spun materials of polyester, polyethylene and the like may also be used. Although layer 12 may take any form capable of exudate transfer, such as perforated polyethylene film and the like, wicking fiber materials are most preferred as they appear to present the best mode of liquid transfer at this time. The material described in Table 1 is commercially available as Microfiber 1515 from the Carl Freudenberg Company of Weinheim, Germany. Fibers having similar wicking characteristics could also be used. The German standard test method DIN 53924 "Velocity of soaking water of textile fabrics" can be used to determine the suitability of materials for the purposes of this invention and is incorporated herein by reference in its entirety.

TABLE I

| CHARACTERISTIC | STANDARD VALUE |
|---|---|
| Construction | Spunbond |
| Bonding type | Thermally bonded endless filaments |
| Fibers | Polypropylene |
| Weight (g/m$^2$) | 15 |
| Thickness (mm) | 0.16 |
| Max. elongation (%) | 60 |
| Max. tensile strength (N/5 cm) | 29 |
| Tear strength (N) | 5.5 |

Layer 14 is the intermediate layer which is comprised of absorptive hydrogel. The formulation is dictated by the need to maximize absorbency without breakdown of the hydrogel while maintaining as thin a profile as possible. Preferably, the hydrogel will be capable of absorbing more than ten times its weight in fluid without breaking down. The high absorbency will minimize the need for frequent dressing changes thereby decreasing the risk of traumatizing the healing wound. Table II illustrates the formulas of three exemplary hydrogels that have been found suitable as layer 14. These hydrogels are based on the polymerization of 2-acrylamido-2-methylpropanesulfonic acid or a salt thereof. Similar hydrogels have been described as electrode materials in U.S. Pat. Nos. 4,391,278 and 4,768,523. The hydrogel may include in the central portion thereof a reinforcing fabric such as a spun bonded polyester. For use as layer 14, a hydrogel thickness of 0.25–0.75 mm will yield the desired minimal profile and a wound dressing that is conformable and easy to maintain over the wound in most instances.

TABLE II

| COMPOSITION (% w/w) | EXAMPLE | EXAMPLE | EXAMPLE |
|---|---|---|---|
| NaAMPS | 49.7 | 43.5 | 37.5 |
| Acrylic Acid | 2.8 | 3.0 | 3.0 |
| Sorbitol | NA | 50.0 | 55.0 |
| PEG 600 | 40 | NA | NA |
| 50% Xanthan Soln. in IPA | NA | 0.5 | NA |
| Silica | 4.5 | NA | 2.5 |
| 1% MBA Soln. | 3.0 | 3.0 | 2.0 |
| Final pH | 6.02 | 6.02 | 6.03 |
| 3% Catalyst | 0.5 | 0.5 | 0.5 |

Layer 16 is the outer layer which may, for example, be an ether type polyurethane film with a thickness of 0.02–0.05 mm. Alternate materials may be used as layer 16, such as an elastomeric polyester (Hytrel™) or a thin polyethylene film. Ideally, the material chosen for layer 16 will be thin, conformable, easy to handle, dimensionally stable and will have a moisture vapor transmission rate (MVTR) sufficient to allow some evaporation of wound exudate from the dressing.

A quantity of adhesive 18 may be included on the exposed peripheral underside of layer 16 in this particular embodiment of the invention. Such adhesives as Monsanto 612 or FLEXcon adhesive H-566 are suitable for this purpose. Adhesive 18 should be hypoallergenic and designed for prolonged use on human skin.

In overall profile, incorporating the specific layer examples described above in the following thicknesses:
layer 12-0.16 mm
layer 14-0.50 mm
layer 16-0.03 mm
will provide a preferred wound dressing having a total profile thickness of about 0.70 mm. Of course, all of these dimensions can be varied to suit any particular situation or purpose.

According to one method for making the dressing of this invention, the hydrogel sheet is preformed by known procedures. For example, the gel forming composition may be cast and cured on a suitable substrate such as Mylar™ polyester. In a second step, layer 12 and layer 16 are laminated to the hydrogel layer. Ideally, the hydrogel will be formulated to be a material with sufficient tack to hold the layers of the laminate together. The hydrogel examples depicted in Table II were found to be sufficiently tacky to maintain the laminated configuration.

Wound complications can occur that are not treated effectively with a simple occlusive dressing. For example, wound infection can be a serious complication of wound healing, sometimes leading to sepsis and death. Therefore, topical medications such as antimicrobials may be a necessary adjunct to the occlusive therapy. Consequently, therapeutic agents such as gentamicin sulfate, erythromycin or neomycin may be included in the hydrogel.

An additional aspect of this invention is aimed at enhancing the rate of wound healing. Polypeptide growth factors were originally defined as agents that promote cell proliferation. It is now known that these proteins also have potent and diverse effects on cell differentiation, motility and matrix synthesis. The role of growth factors in the repair of soft tissue wounds is of great clinical interest. However, the current challenge, considering their short in vivo half-lives, is to develop effective methods for delivery of growth factors to chronic wounds. The porous polymer layer 12 may be considered a delivery vehicle for such agents. In particular, two delivery methods are embodied in this portion of the invention. The first method is the attachment of exogenous growth factors or other biologically active molecules such as fibronectin or hyaluronic acid to the wound-contacting layer 12. These agents could be chemically coupled to layer 12 by various interactions including ionic bonding or covalent attachment. The second method is the chemical modification of layer 12 so as to provide a surface which would stabilize endogenous growth factors present in the wound exudate. An example of this second method is the covalent attachment of heparin to layer 12 to stabilize endogenous heparin binding growth factors such as fibroblast growth factor.

In addition to surface modification, another key factor of this aspect of the invention is the presence of openings in layer 12 which not only allow for fluid transport of exudate from the wound to the hydrogel but actually draw or wick the fluid to the hydrogel. This maximizes the interaction of the wound with the biologically active surface of layer 12. As the wound exudate is drawn through the coated layer 12 to the hydrogel, growth factors or other biologically active molecules will bind to the surface of layer 12. This binding can serve to localize the molecules within the wound environment and may protect the growth factors or other agents from denaturation and degradation.

A number of coatings have recently been developed with the goal of surface modifying layer 12 polymers. One method involves grafting hydrogel monomers onto the polymer surface via ceric ion initiation. The hydrogel coating provides a suitable surface for subsequent attachment of biologically active molecules. Plasma treatment, corona treatment and direct chemical methods can be used to create a functional surface for subsequent attachment of biologically active molecules to a polymer surface. The following examples illustrate this portion of the invention.

This following example illustrates one method that has been used to covalently attach heparin to a polyurethane surface. Polyurethane may be used as layer 12. The heparin coated surface is of interest because biomolecules such as insulin, platelet derived growth factor and fibroblast growth factor (FGF) will bind specifically to the modified surface. Binding to heparin protects FGF from inactivation and localizes the growth factor within the wound environment. In this example, the polyurethane was perforated and used as layer 12 of a composite wound dressing for testing on an animal model of partial thickness wounds. The heparin coating technique begins with the graft copolymerization of acrylamide (AAm) and n-(3-aminopropyl)methacrylamide (APMA) monomers onto the polyurethane surface with CeIV ion. The amount of graft copolymerization of APMA and AAM that takes place can be measured by staining the polyurethane surface with ponceau S dye. The dye ionically associates with primary amines on the aminated surface. After staining, the dye is released from the surface using SDS and quantified spectrophotometrically at 520 nm. The aminated surface is then used for coupling heparin. The heparin is oxidized using sodium m-periodate to yield reactive aldehyde groups. The aldehyde groups are then attached to primary amino groups in the grafted APMA/AAm through reductive amination (Schiff base reaction). Sodium cyanoborohydride is used to stabilize the imine linkages.

Figure 3:
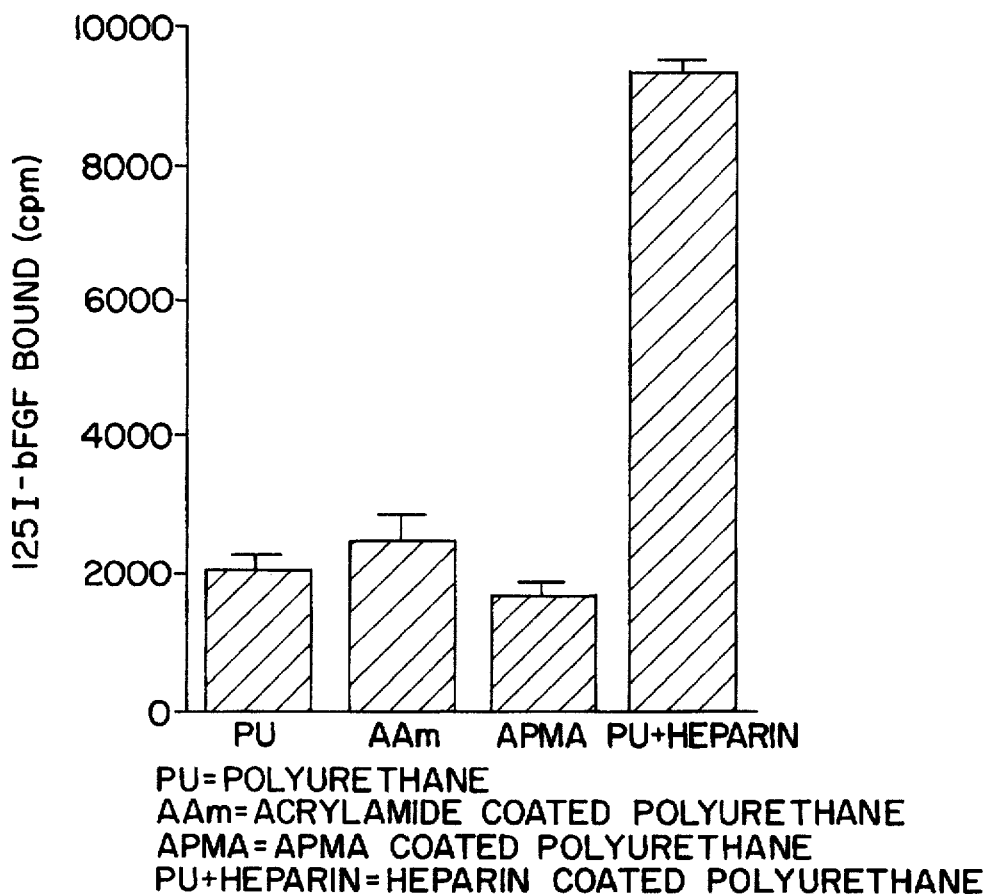
FIG. 3 is a bar graph showing the level of basic fibroblast growth factor binding to a heparin coated form of layer 12 in FIGS. 1 and 2.

The amount of heparin attached to the polyurethane can be measured by staining the surface with toluidine blue dye. The dye is released from the surface using SDS and is quantified spectrophotometrically at 640 nm. The heparin activity of the surface is measured using a thrombin-ATIII activation assay. As shown in FIG. 3, the amount of basic fibroblast growth factor (bFGF) that binds to the heparinized polyurethane was measured using radiolabeled bFGF. In these studies, polyurethane (both treated and untreated) was cut to fit into 24 well tissue culture plates. The samples were incubated for 60 min at 25° C. in a phosphate buffered saline solution that contained 1% serum albumin, 0.04 nM bFGF and 0.04 nM $^{125}$I-bFGF. The samples were rinsed three times (15 min each) in phosphate buffered saline, air dried and counted in a Beckman gamma counter.

Figure 4:
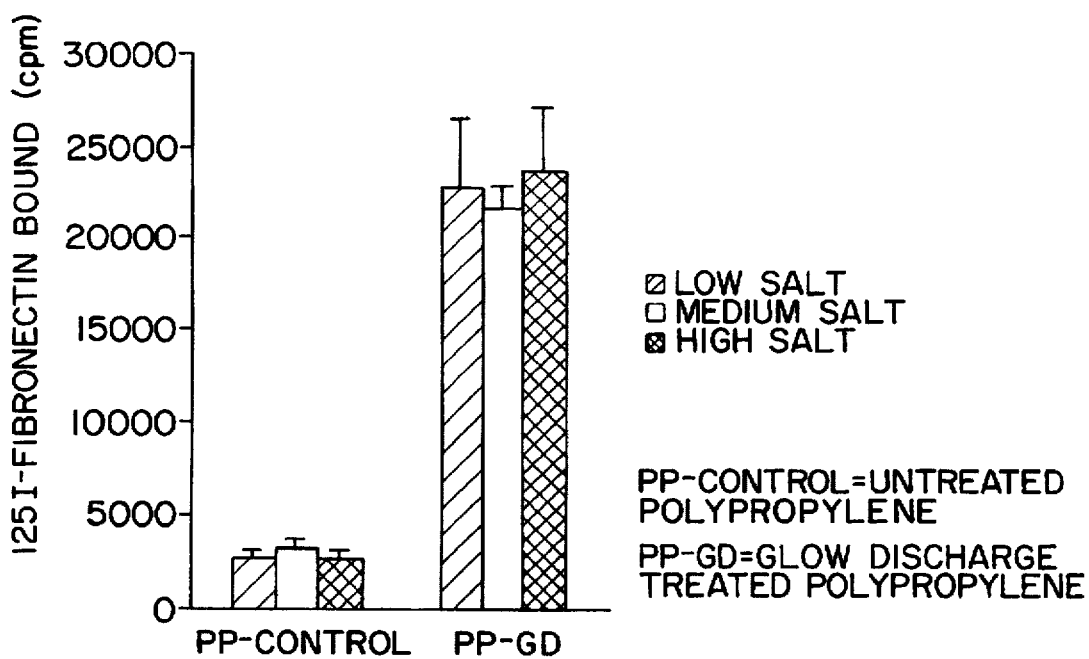
FIG. 4 is a bar graph showing the level of fibronectin binding to a plasma treated form of layer 12 in FIGS. 1 and 2.

This example illustrates a method that has been used to attach fibronectin to the thermally bonded spun web polypropylene material described in Table I. Fibronectin, an adhesion protein found in blood and many tissues, is deposited at the wound interface after injury. Fibronectin has been shown to promote keratinocyte migration. However, it has been reported that partial degradation of fibronectin occurs in wound fluid samples from patients with venous stasis and diabetic ulcers. It would be expected, therefore, that exogenous delivery of a stable form of fibronectin would promote wound healing. Indeed, in recent clinical trials topical application of fibronectin was found to increase epithelialization of venous stasis ulcers. In the present example, glow discharge (exposure of the material to an ionized gas) in the presence of $NH_3$ was used to create positively charged functional groups on the polypropylene. The presence of positive charges was confirmed by staining with ponceau S dye. As shown in FIG. 4, the ability of fibronectin to bind to the glow discharge treated polypropylene was measured using $^{125}$I-labeled fibronectin. Samples of untreated polypropylene and glow discharge treated polypropylene were incubated for 2 hrs at 37° C. in phosphate buffered saline (pH 7.4) that contained 0.01 µg/mL fibronectin, 0.1 ng/mL $^{125}$I-labeled fibronectin and 1 mg/mL bovine serum albumin. After the 2 hr incubation, the samples were rinsed three times (30 min each) in either a low salt (13.8 mM NaCl) buffer, a medium salt buffer (138 mM NaCl) or a high salt buffer (600 mM NaCl). The samples were blotted dry and counted in a Beckman gamma counter.

The examples described herein and the disclosure are intended to be illustrative and not exhaustive. These examples and description will suggest many variations and alternatives to one of ordinary skill in this art. All of these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A wound dressing for use with exuding wounds comprising:

an outer vapor permeable layer permitting transpiration of fluid from the wound dressing;

an intermediate layer of hydrogel adapted for absorbing wound exudate;

a wound-contacting layer for separating the intermediate hydrogel layer from the wound, the layer of hydrogel between the wound-contacting layer and the outer layer;

wicking means for conducting exudate from the wound to the hydrogel; and a therapeutic agent retained in said wound dressing by the wound-contacting layer.

2. The wound dressing of claim 1 wherein the intermediate layer and the wicking layer means are of smaller dimension than the outer layer whereby peripheral portions of the underside of the outer layer are exposed.

3. The wound dressing of claim 2 also comprising adhesive means on the exposed peripheral portions of the outer layer.

4. The wound dressing of claim 1 wherein the therapeutic agent is in the wound-contacting layer.

5. The wound dressing of claim 4 wherein the therapeutic agent comprises biologically active molecules bound to the wound-contacting layer.

6. The wound dressing of claim 5 wherein the molecules are bound by covalent attachment.

7. The wound dressing of claim 6 wherein the wound-contacting layer is comprised of a plurality of polymeric fibers and the molecules are bound to the fibers.

8. The wound dressing of claim 7 wherein the therapeutic agent is heparin with a growth factor attached to the heparin.

9. The wound dressing of claim 8 wherein the growth factor is basic fibroblast growth factor.

10. The wound dressing of claim 7 wherein the therapeutic agent is fibronectin.

* * * * *